(12) United States Patent
Lu et al.

(10) Patent No.: US 9,841,411 B2
(45) Date of Patent: Dec. 12, 2017

(54) AMMONIA GAS SENSOR BASED ON SQUARIC ACID DERIVATIVE, PREPARATION METHOD AND APPLICATION THEREOF

(71) Applicant: Soochow University, Suzhou, Jiangsu (CN)

(72) Inventors: Jianmei Lu, Jiangsu (CN); Jinghui He, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 15/405,370

(22) Filed: Jan. 13, 2017

(65) Prior Publication Data
US 2017/0205383 A1 Jul. 20, 2017

(30) Foreign Application Priority Data

Jan. 14, 2016 (CN) .......................... 2016 1 0024126

(51) Int. Cl.
G01N 27/04 (2006.01)
G01N 27/07 (2006.01)
G01N 33/00 (2006.01)
C23C 14/24 (2006.01)

(52) U.S. Cl.
CPC ....... G01N 33/0054 (2013.01); C23C 14/243 (2013.01); G01N 27/04 (2013.01)

(58) Field of Classification Search
CPC ... G01N 33/0054; G01N 27/04; C23C 14/243
See application file for complete search history.

(56) References Cited

PUBLICATIONS

Xiao, Xin, et al. "Ion-in-Conjugation: Squaraine as an Ultrasensitive Ammonia Sensor Material." Small 13.2 (2017).*

* cited by examiner

*Primary Examiner* — Robert Eom
(74) *Attorney, Agent, or Firm* — SZDC Law P.C.

(57) ABSTRACT

An ammonia gas sensor based on a squaric acid derivative includes an interdigital electrode and a coating material. The coating material is a squaric acid derivative of formula I, and said coating material is coated on said interdigital electrode through a vacuum coating process, and a thickness of said coating material is 100-200 nm.

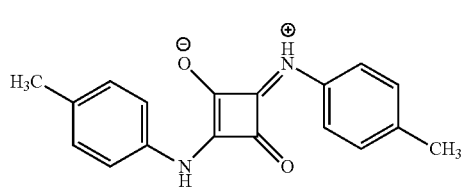

I

8 Claims, 4 Drawing Sheets

AMMONIA GAS SENSOR BASED ON SQUARIC ACID DERIVATIVE, PREPARATION METHOD AND APPLICATION THEREOF

This application claims priority to Chinese Patent Application No. 201610024126.1, filed Jan. 14, 2016, which is incorporated by reference for all purposes as if fully set forth herein.

TECHNICAL FIELD

The invention belongs to the technical field of organic semiconductor material, in particular to an ammonia gas sensor based on squaric acid derivative, its preparation method and its use in air quality detection, especially in ammonia gas detection.

BACKGROUND ART

With the increasing environmental pollution, the environmental problems become more and more concerned by the society, more particularly, closely related to human health, the air environmental issues in the small environment is much more concerned. Ammonia is a colorless gas with highly irritating odor, which is lighter in density than air (the relative specific gravity is about 0.5), and its lowest sensible concentration to the human body is 5.3 ppm. When the ammonia contacts with the body's skin tissue, it will not only stimulate the role, but also will corrode the skin. Ammonia can denature proteins through absorbing water in the skin, so as to saponify the fat in the tissues, and to damage cell membrane structure. As ammonia has a high solubility, it will mainly result in stimulation and corrosion to the upper respiratory tract of animal or human body, to weaken the body's ability to resist disease. When its concentration is too high, it will induce cardiac arrest and respiratory arrest by the reflex of trigeminal nerve endings. However, the common ammonia gas sensor has high detection limit, poor selectivity, and complicated manufacture process. Therefore, a new ammonia sensor with low detection limit, high selectivity and simple preparation process is urgently needed.

INVENTION CONTENT

According to such situation, the present invention uses a squaric acid derivative MSA (whose structure is shown below) to prepare an ammonia gas sensor and detects ammonia gas of different concentrations by observing changes in the I-V curve of the sensor at different gas concentrations. In order to detect the selectivity of the sensor, the invention also detects the organic vapors at the same temperature. The results show that the sensor has the advantages of good stability, low detection limit and high selectivity, and the detection level can reach ppb level, The preparation process of the sensor is simple, so it has a strong commercial value and broad market prospects.

More specifically, the present invention adopts the following technical scheme:

The application of squaric acid derivative of formula I in the preparation of ammonia gas sensors,

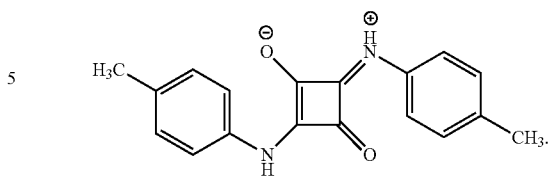

The ammonia gas sensor based on a squaric acid derivative comprises an interdigital electrode and a coating material, said coating material is a squaric acid derivative of the formula I mentioned above, said coating material is coated on said interdigital electrode through the vacuum coating process, and the thickness of said coating material is 100-200 nm.

It is preferred that in the ammonia gas sensor based on a squaric acid derivative, said interdigitated electrode takes a layered structure of silicon, silicon dioxide (with the thickness of 270-330 nm, preferably 300 nm) and chromium (with the thickness of 9-11 nm, preferably 10 nm) in bottom-up sequence as a base, with the gold electrode (with the thickness of 90-110 nm, preferably 100 nm) arranged on said base; the interdigital width of said interdigital electrode is 3-8 um (preferably 5 um), the spacing of the interdigitals is 2-5 um (preferably 3 um).

The ammonia gas sensor based on a squaric acid derivative mentioned above is prepared through the preparation method comprising the steps as follows:

1) cleaning a substrate, and fixing the interdigital electrode on the substrate;

2) placing the substrate having the interdigital electrode fixed in step 1) into a vacuum coating apparatus, and charging the squaric acid derivative of the formula I into the vacuum coating apparatus as a coating material;

3) setting the vacuum deposition parameters as following: the deposition speed is 5 to 6 Å/s, the deposition pressure is 1E-6 to 1E-5 mbar, the deposition temperature is 120 to 140° C.;

4) after the parameter setting is completed, turning on the pressure reducing device to reduce the pressure inside the chamber of the vacuum deposition apparatus, when the chamber pressure is less than 5.0 mbar, turning on the molecular pump, when the pressure reaches the deposition pressure, beginning to evaporate the film until the desired thickness is reached, to get the ammonia gas sensor based on a squaric acid derivative.

Preferably, in the preparation method, the fixing in step 1) is accomplished by means of double-sided adhesive bonding.

Preferably, in the preparation method, the vacuum coating apparatus in step 2) is a vacuum coating machine.

Preferably, in the preparation method, the vacuum deposition parameters in step 3) is set as follows: the deposition speed is 5 Å/s, the deposition pressure is 1E-5 mbar, the deposition temperature is 120° C.

Preferably, in the preparation method, the pressure reducing device in step 4) is a vacuum pump.

The application of said ammonia gas sensor based on a squaric acid derivative in air quality checking, especially in the detection of ammonia.

Compared with the existing technology, using the above technical scheme of the invention has the following advantages:

(1) The device is easy to prepare, and the operation is simple;

(2) Selectivity is high, the intensity of the sensor for ammonia is much higher than other molecules;

(3) High sensitivity, produce current response to minimal change of the concentration of ammonia;

(4) The lowest detection limit is very low, can test ppb level of ammonia.

DETAILED DESCRIPTIONS

The technical solution of the present invention will be further described hereinafter with reference to the accompanying drawings and specific examples. Unless otherwise indicated, reagents, materials, instruments, etc., used in the examples below may be obtained commercially.

Example 1: Synthesis of MSA and Preparation of Ammonia Gas Sensor (1) Synthesis of MSA:

p-toluidine (1.80 g, 8.76 mmol) and squaric acid (1.88 g, 17.52 mmol) are weighed and added into an equal volume mixture of n-butanol and toluene (40 mL). The reaction mixture is heated and refluxed for 12 h. After filtration, the solid is washed three times with chloroform and n-hexane and dried in a vacuum oven at 60° C. for 24 h to give a bright yellow solid MSA (2.77 g, yield 93.75%).

The corresponding physical and chemical identification data are as follows:

$^1$H-NMR (400 MHz, DMSO-d$_6$) δ 9.81 (s, 1H), 9.16 (s, 1H), 7.52 (d, J=7.6 Hz, 2H), 7.38 (d, J=7.6 Hz, 2H), 7.18 (d, J=7.3 Hz, 2H), 6.97 (d, J=7.7 Hz, 2H), 2.27 (s, 3H), 2.19 (s, 3H).

Figure 1:
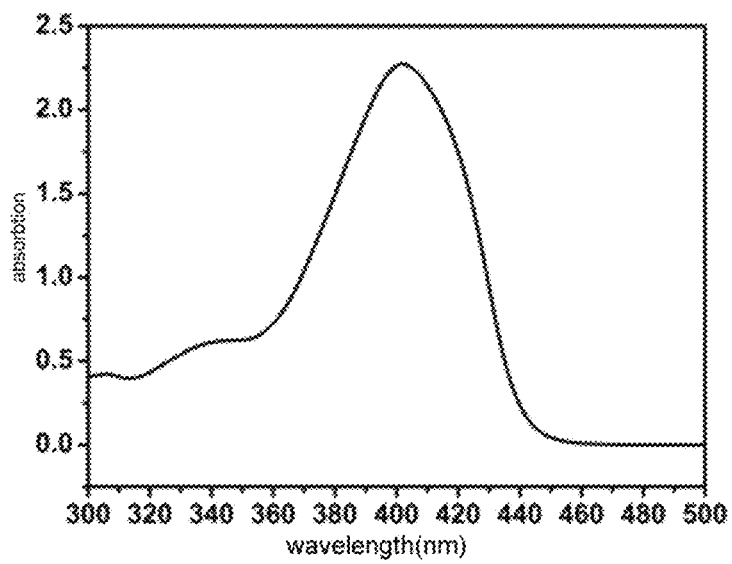
FIG. 1 shows the UV spectra of MSA molecules.

UV spectrum shown in FIG. 1.

Figure 2:
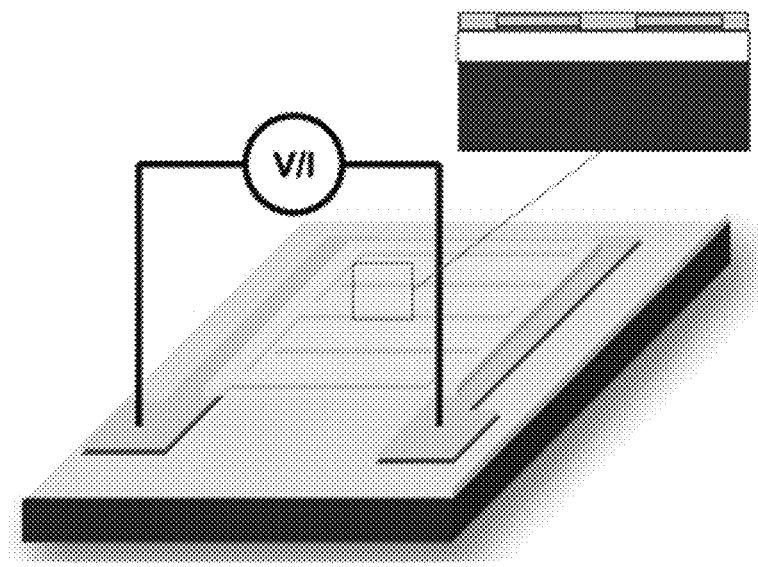
FIG. 2 shows the structure of the sensor based on MSA thin film.

(2) Preparation of the Sensor:

(a) Clean the glass substrate and bond the interdigital electrode on the substrate with a double-sided adhesive. The interdigitated electrode takes a layered structure of silicon, silicon dioxide (300 nm) and chromium (10 nm) in bottom-up sequence as a base, with the gold electrode (100 nm) arranged on; the interdigital width is 5 um, the spacing of the interdigitals is 3 um;

(2) Place the substrate having the interdigital electrode fixed in step 1) into a vacuum coating machine, weigh 35 mg of MSA and place in a quartz crucible, put the crucible into the vacuum coating machine for use later;

(3) Set the vacuum deposition parameters as following: the deposition speed is 5 Å/s, the deposition pressure is 1E-5 mbar, the deposition temperature is 120° C.;

(4) After the parameter setting is completed, turn on the vacuum pump to reduce the pressure inside the chamber of the vacuum coating machine, when the chamber pressure is less than 5.0 mbar, turn on the molecular pump (If the molecular pump were turned on when the pressure is too high, the molecular pump would be damaged so that the deposition pressure is hard to reach, and the quality of the film will be poor), when the pressure reaches 1E-5 mbar, begin to evaporate the film until the thickness reaches 100 nm, to get the ammonia gas sensor based on a squaric acid derivative. The structure of the sensor is shown in FIG. 2.

Figure 3:
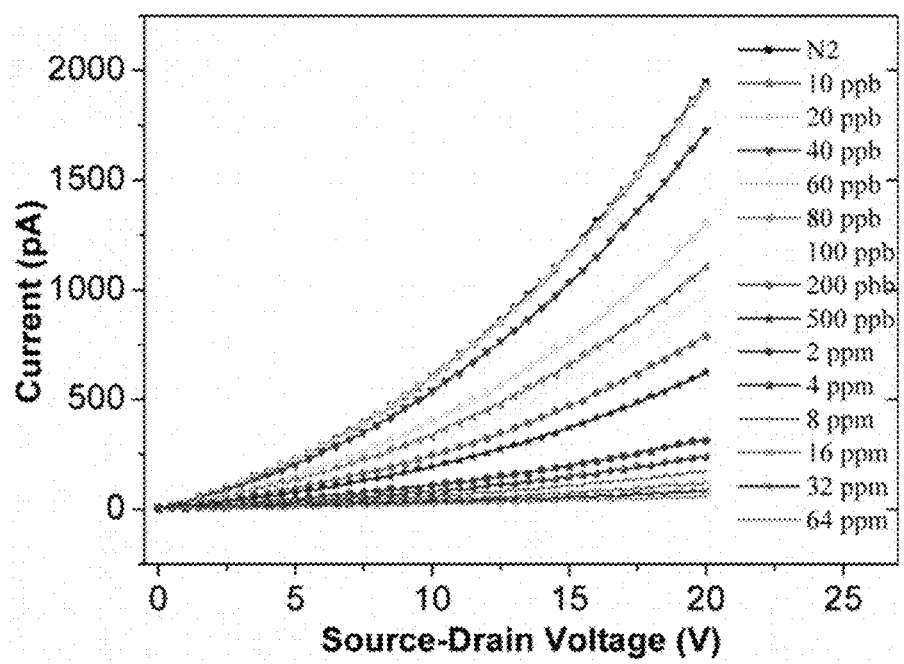
FIG. 3 shows the I/V curve of the ammonia-gas concentration of 10 ppb to 64 ppm for the sensor based on the MSA thin film.

Example 2: Measurement of I-V Curves of MSA Thin Film Sensors at Different Gas Concentrations The measurement of the IV curve of the MSA thin film sensor at different gas concentrations was carried out by diluting 1000 ppm of ammonia gas with nitrogen to obtain ammonia gas of different concentrations and maintaining the gas concentration at a desired concentration by means of a dynamic gas distribution device. As shown in FIG. 3.

As can be seen in FIG. 3, the MSA sensor has a different current response for ammonia at different concentrations. The higher the concentration, the smaller the corresponding current, but with the concentration increased to 4 ppm or more, the change of the current value is smaller, to reach balance almostly.

Example 3: Determination of Resistance Change of MSA Thin Film Sensor at Different Gas Concentrations In order to explore the sensing regularity of the MSA device, the present invention tests the relationship between the resistance change ($(I_0-I/I)$) of the device and the change in gas concentration and the relationship between the current and the concentration, standard ammonia gas of 1000 ppm is diluted with high purity nitrogen to different concentrations, and the device is placed in different concentrations of gas atmosphere, the test current changes and converted to resistance changes, the results shown in FIG. 4.

Figure 4:
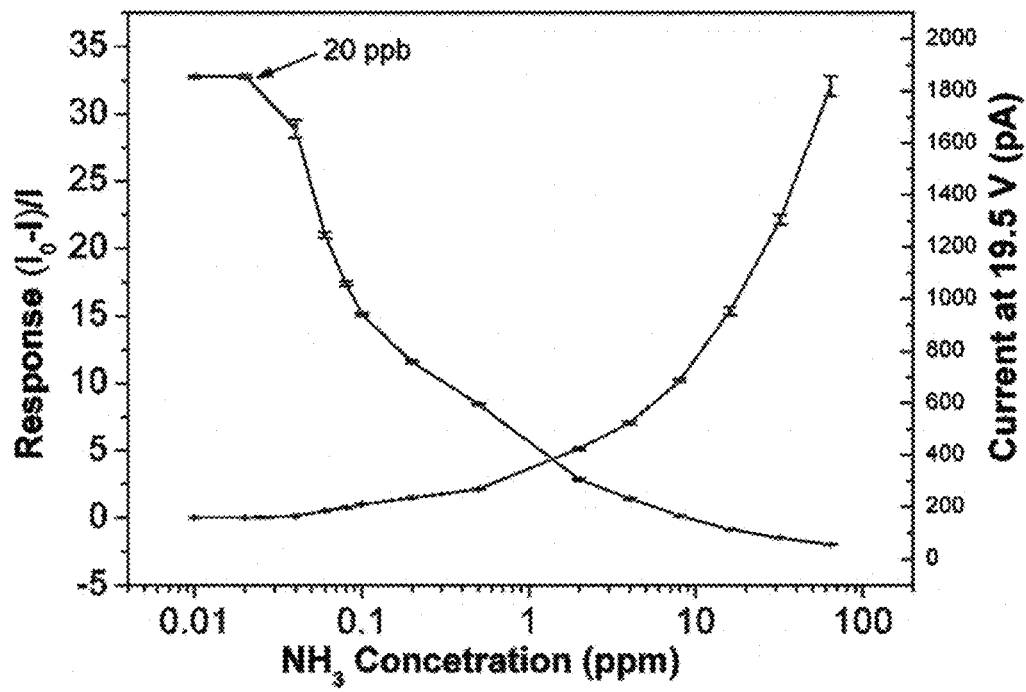
FIG. 4 shows the resistance changes of the sensor based on the MSA film to ammonia concentration of 10 ppb to 64 ppm.

It can be seen from FIG. 4 that with the increasing concentration of ammonia, the resistance of the device is also increasing, the current value (voltage 19.5 V) decreased significantly, and has a certain function relation.

Example 4: Recovery of the MSA Thin Film Sensor

The voltage is set to 10 V, the device is connected to ammonia with the concentration of 60 ppb, after 1 min, provide nitrogen to the device, and then followed by different concentrations of ammonia and nitrogen, for testing the recoverability of the device. The results are shown in FIG. 5.

Figure 5:
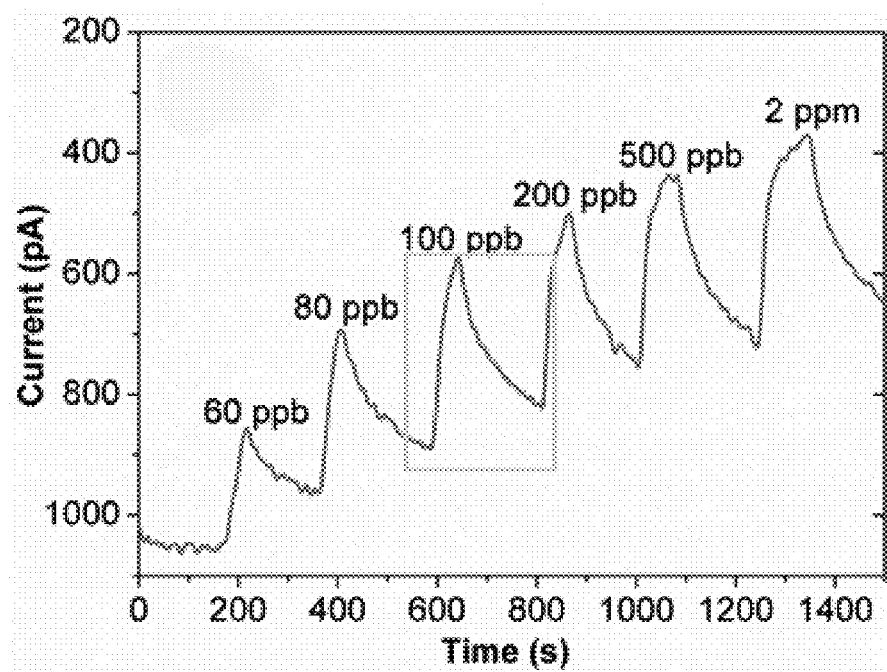
FIG. 5 shows the recoverability of the sensor based on the MSA film.

As can be seen from FIG. 5, the current decreases with the addition of ammonia at different concentrations (60 ppb to 2 ppm), but the current rapidly rises to the baseline position after passing in nitrogen. It can be proved, MSA thin film sensor is recoverable, suitable for long-term and stable detection of ammonia in the air.

Example 5: Selectivity Test for MSA Sensor

Figure 6:
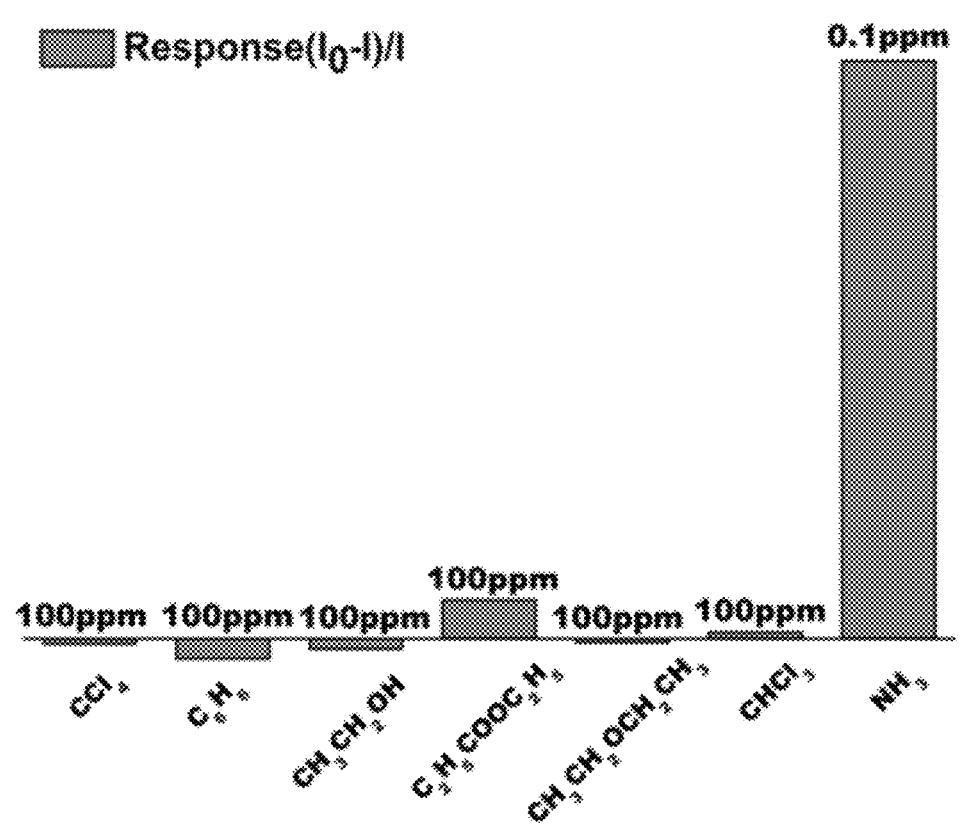
FIG. 6 shows the selectivity of the MSA thin film based sensor.

In order to test the selectivity of the gas sensor, 100 ppm of ethanol, carbon tetrachloride, chloroform, ethyl ether, benzene, ethyl acetate and other gases are selected at the same temperature to test the response of the device to the intensity, the results shown in FIG. 6.

As can be seen in FIG. 6, the MSA thin film sensor of the present invention has a low response strength to a high concentration (100 ppm) of ethanol, carbon tetrachloride and other gases, with little or no response, and for very low concentrations (0.1 ppm) of ammonia, the response intensity can reach a very high level. Thus, the MSA thin-film sensor of the present invention is not only low in detection limit but also high in selectivity.

In summary, the present invention realizes the detection of ammonia gas at very low concentration by making a simple acid-type film sensor of simple structure and high selectivity, and solves the problem that the present lack of low detection limit The ammonia gas sensor based on the squaric acid derivative of the invention has a high application value for the future treatment of air pollution.

The invention claimed is:

1. An ammonia gas sensor based on a squaric acid derivative, comprising an interdigital electrode and a coating material,
   wherein said coating material is a squaric acid derivative of formula I:

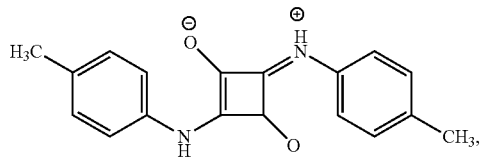

and said coating material is coated on said interdigital electrode, and a thickness of said coating material is 100-200 nm.

2. The ammonia gas sensor based on a squaric acid derivative according to claim 1, wherein
   said interdigital electrode takes a layered structure of silicon, silicon dioxide and chromium in bottom-up sequence as a base, with a gold electrode arranged on said base;
   said silicon dioxide is 270-330 nm thick, said chromium is 9-11 nm thick, and said gold electrode is 90-110 nm thick.

3. The ammonia gas sensor based on a squaric acid derivative according to claim 1, wherein the interdigital electrode comprises a plurality of interdigitals; each interdigital has a width of 3-8 um; and adjacent interdigitals are spaced apart by 2-5 um.

4. A method of preparing an ammonia gas sensor based on a squaric acid derivative comprising the steps as follows:
   1) cleaning a substrate, and fixing an interdigital electrode on the substrate;
   2) placing the substrate having the interdigital electrode fixed in step 1) into a vacuum coating apparatus, and charging a squaric acid derivative of formula I into the vacuum coating apparatus as a coating material;

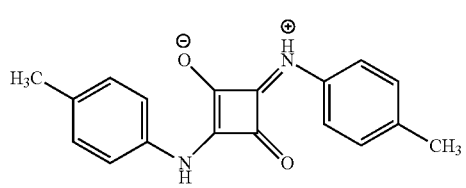

3) setting vacuum deposition parameters as following: deposition speed being set between 5 and 6 Å/s, deposition pressure being set between 1E-6 and 1E-5 mbar, deposition temperature being set between 120 and 140° C.;
   4) after performing step 3), turning on a pressure reducing device to reduce pressure inside a chamber of the vacuum deposition apparatus, turning on a molecular pump to reduce the pressure inside the chamber to equal or less than 1E-5 mbar, and beginning to evaporate the coating material until a thickness of 100-200 nm is reached, to get the ammonia gas sensor based on a squaric acid derivative.

5. The method according to claim 4, wherein the fixing in step 1) is accomplished by double-sided adhesive bonding.

6. The method according to claim 4, wherein said vacuum coating apparatus in step 2) is a vacuum coating machine.

7. The method according to claim 4, wherein the vacuum deposition parameters in step 3) is set as follows: the deposition speed being set at 5 Å/s, the deposition pressure being set at 1E-5 mbar, the deposition temperature being set at 120° C.

8. The method according to claim 4, wherein the pressure reducing device in step 4) is a vacuum pump.

* * * * *